(12) United States Patent
Curren et al.

(10) Patent No.: US 10,173,951 B2
(45) Date of Patent: Jan. 8, 2019

(54) SIDE RECTIFIER COLUMN FOR OLEFIN AND DILUENT RECOVERY

(71) Applicant: Chevron Phillips Chemical Company LP, The Woodlands, TX (US)

(72) Inventors: Joseph A. Curren, Kingwood, TX (US); Ralph W. Romig, Kingwood, TX (US); Ji Xian Loh, Houston, TX (US); Timothy O. Odi, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 218 days.

(21) Appl. No.: 15/264,008

(22) Filed: Sep. 13, 2016

(65) Prior Publication Data
US 2018/0072639 A1    Mar. 15, 2018

(51) Int. Cl.
| | | |
|---|---|---|
| *B01D 3/00* | (2006.01) | |
| *C07C 7/04* | (2006.01) | |
| *C08F 210/16* | (2006.01) | |
| *C10B 57/04* | (2006.01) | |
| *C10B 47/06* | (2006.01) | |
| *B01L 3/00* | (2006.01) | |

(52) U.S. Cl.
CPC .................... *C07C 7/04* (2013.01); *B01L 3/00* (2013.01); *C08F 210/16* (2013.01); *C10B 47/06* (2013.01); *C10B 57/04* (2013.01)

(58) Field of Classification Search
CPC .................... C07C 7/04; B01D 3/00
See application file for complete search history.

(56) References Cited

U.S. PATENT DOCUMENTS

| | | | | |
|---|---|---|---|---|
| 3,364,139 | A * | 1/1968 | Kunesh ..................... | C07C 7/04 203/39 |
| 4,230,533 | A * | 10/1980 | Giroux ..................... | B01D 3/14 196/132 |
| 5,953,936 | A * | 9/1999 | Agrawal ................ | B01D 3/146 62/630 |
| 5,970,742 | A * | 10/1999 | Agrawal ................ | B01D 3/146 62/630 |
| 6,514,387 | B1 * | 2/2003 | Emmrich ............... | B01D 3/141 196/111 |
| 6,551,465 | B1 * | 4/2003 | Van Zile ................. | B01D 3/14 159/44 |
| 6,559,247 | B2 | 5/2003 | Kufeld et al. | |
| 7,528,290 | B2 * | 5/2009 | Zimmermann ........ | B01D 1/007 202/152 |
| 7,629,421 | B2 | 12/2009 | Tait et al. | |
| 7,741,430 | B2 | 6/2010 | Walworth | |
| 7,759,457 | B2 | 7/2010 | Walworth | |
| 8,017,701 | B2 | 9/2011 | McElvain et al. | |

(Continued)

FOREIGN PATENT DOCUMENTS

EP    1791875 B1    3/2013

OTHER PUBLICATIONS

Foreign communication from the corresponding International Application No. PCT/US2017/050230, International Search Report and Written Opinion, dated Dec. 21, 2017, 11 pages.

*Primary Examiner* — Jonathan Miller
(74) *Attorney, Agent, or Firm* — Conley Rose, P.C.

(57) ABSTRACT

Processes and systems for olefin and diluent recovery utilizing one or more side columns, including a side rectifier column and/or a side degassing column, in combination with a heavies column.

20 Claims, 4 Drawing Sheets

(56) References Cited

U.S. PATENT DOCUMENTS

| | | | |
|---|---|---|---|
| 8,128,877 B2 | 3/2012 | McElvain et al. | |
| 8,303,899 B2 | 11/2012 | McElvain et al. | |
| 8,569,433 B2 | 10/2013 | McElvain et al. | |
| 8,653,206 B2 | 2/2014 | Gessner et al. | |
| 8,765,884 B2 | 7/2014 | McElvain et al. | |
| 9,096,694 B1 | 8/2015 | Gupta et al. | |
| 9,221,920 B2 | 12/2015 | McElvain et al. | |
| 2001/0018499 A1 | 8/2001 | Marissal et al. | |
| 2003/0181772 A1* | 9/2003 | Meyer | B01D 3/141 585/324 |
| 2003/0191251 A1 | 10/2003 | McGrath | |
| 2009/0288939 A1* | 11/2009 | Smith | B01D 3/14 202/158 |
| 2009/0288940 A1* | 11/2009 | Smith | B01D 3/14 203/71 |
| 2012/0103013 A1* | 5/2012 | King | B01D 3/141 62/625 |
| 2012/0264911 A1* | 10/2012 | Mills | B01D 3/009 528/501 |

* cited by examiner

United States Patent 10,173,951 B2

SIDE RECTIFIER COLUMN FOR OLEFIN AND DILUENT RECOVERY

TECHNICAL FIELD

The present disclosure relates to olefin and diluent recovery processes downstream of a polymerization reactor.

BACKGROUND

Polyolefins can be prepared by polymerization of olefins in one or more reactors in which feed materials such as diluent, monomer, comonomer and catalyst are introduced. The polymerization reaction within the reactor yields one or more solid polyolefins in a polymerization product. The solid polyolefin can be recovered, and remaining portions of the polymerization product (e.g., residual monomer, residual comonomer, diluent) can be further processed, typically downstream from the reactor in generally complex recovery systems. An ongoing need exists for alternative and/or improved techniques for processing the remaining portions of the polymerization product.

SUMMARY

Disclosed herein is a process comprising feeding isobutane, 1-hexene, and optionally one or more of hydrogen, nitrogen, ethane, and ethylene from one or more polymerization reactors to a feed stage of a heavies column, receiving isobutane and 1-hexene from an intermediate stage of the heavies column into a side rectifier column, the intermediate stage being between the feed stage and a recycle hexene takeoff stage of the heavies column, recovering olefin-free isobutane from the side rectifier column, recycling a first portion of the olefin-free isobutane to the side rectifier column as reflux, and recycling a second portion of the olefin-free isobutane to a polymerization process.

Also disclosed herein is a process comprising feeding a fresh feed stream comprising fresh isobutane, fresh 1-hexene, and volatile components to a side degassing column, the side degassing column being positioned internally of a heavies column between a feed stage and a recycle hexene takeoff stage of the heavies column, recovering the volatile components from an overhead stream of the side degassing column, recycling a liquid phase recovered from the overhead stream of the side degassing column back to the side degassing column as reflux, recovering 1-hexene in a bottoms stream of the side degassing column, and flowing the bottoms stream of the side degassing column to a location external of the heavies column via the recycle hexene takeoff stage.

Further disclosed herein is an olefin and diluent recovery system for use with an olefin polymerization reactor system, the olefin and diluent recovery system comprising a feed stream comprising isobutane, 1-hexene, and optionally one or more of hydrogen, ethane, nitrogen, and ethylene, a heavies column receiving the feed stream and separating the feed stream into an overhead stream comprising isobutane and into a heavies purge bottoms stream comprising purge heavies, a side rectifier column receiving isobutane and 1-hexene from an intermediate stage of the heavies column, the intermediate stage being between a feed stage and a recycle hexene takeoff stage of the heavies column, and an olefin-free isobutane stream flowing from the side rectifier column.

Further disclosed herein is an olefin and diluent recovery system for use with a olefin polymerization reactor system, the olefin and diluent recovery system comprising a first feed stream comprising isobutane and 1-hexene, a heavies column receiving the first feed stream and separating the first feed stream into an overhead stream comprising isobutane and ethylene and a heavies purge bottoms stream comprising purge heavies, a second feed stream comprising fresh isobutane, fresh 1-hexene, and volatile components, and a side degassing column receiving the second feed stream, the side degassing column being positioned internally of the heavies column and utilizing heat generated by a reboiler of the heavies column to separate the volatile components from the fresh isobutane and fresh 1-hexene received from the second feed stream.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
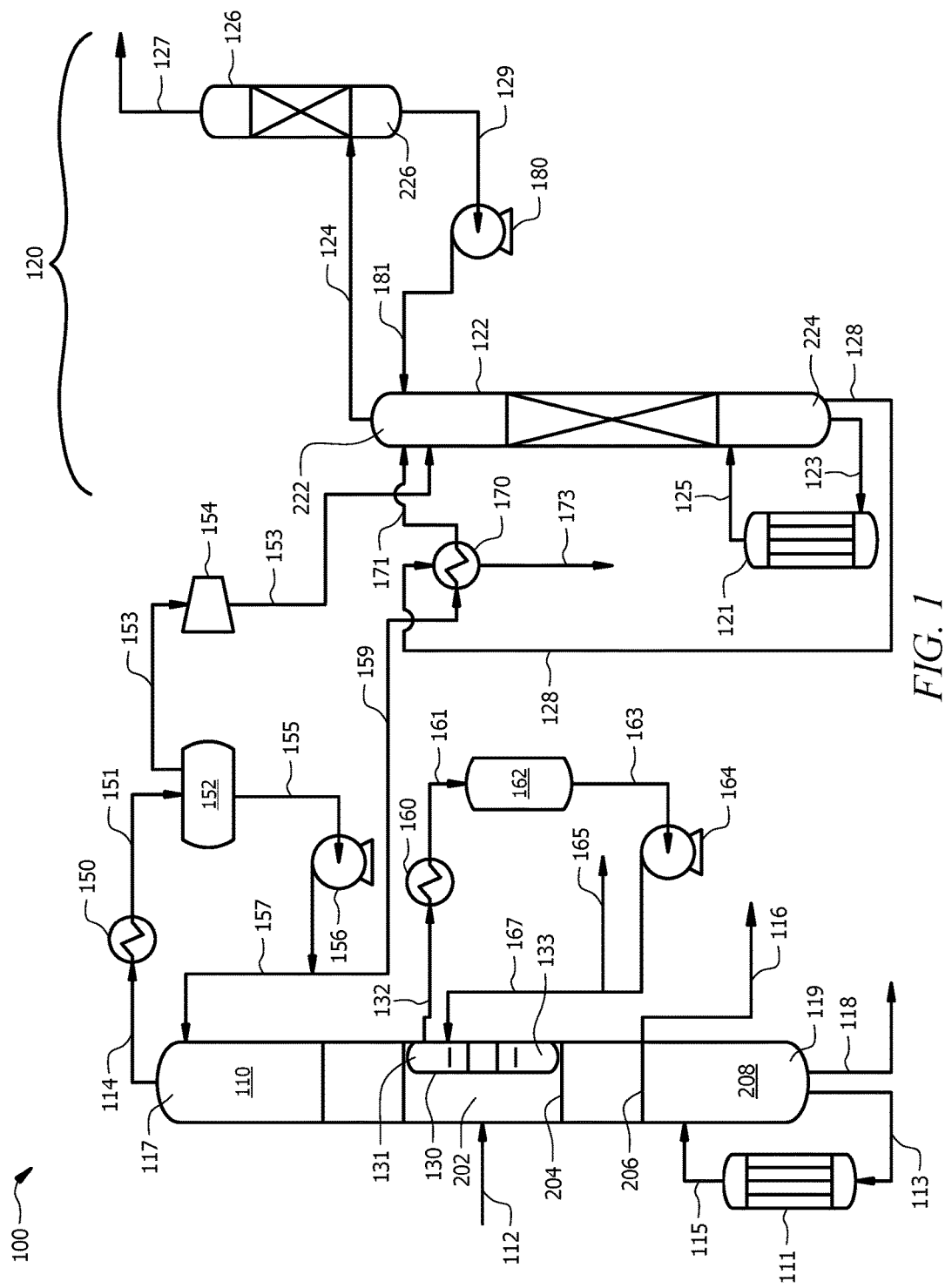
FIG. 1 illustrates an exemplary process flow diagram of an olefin and diluent recovery system in accordance with aspects of the disclosure which utilizes a side rectifier column in combination with a heavies column to recover olefin-free diluent.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The figures described above and the written description of specific structures and functions below are not presented to limit the scope of what Applicants have invented or the scope of the appended claims. Rather, the figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the figures and are not intended to limit the scope of the invention or the appended claims.

Disclosed herein are systems and processes for diluent recovery, for example downstream of a polyolefin polymerization process employing monomer, comonomer, diluent, and a catalyst system. The systems and processes can be configured for use in an olefin polymerization reactor system. The terms "configured for use" or "adapted for use" and similar language is used herein to reflect that the particular recited structure or procedure is used in an olefin polymerization system or process. For example, unless otherwise specified, a particular structure "configured for use" means it is "configured for use in an olefin polymerization reactor system" and therefore is designed, shaped, arranged, constructed, and/or tailored to effect an olefin polymerization, as would have been understood by the skilled person.

The disclosed systems and processes generally utilize a heavies column upstream of a lights column to recover one or more olefins, olefin-free diluent, and recycle-grade diluent. Olefin-free diluent can be recovered using a side rectifier column in combination with the heavies column instead of using the lights column. Recycle-grade diluent subsequently can be recovered using the lights column, which needs no side stream in accordance with the present disclosure. Additionally, light gases can be recovered using a side degassing column in combination with the heavies column rather than using the lights column. By shifting the manner of recovery of components (i.e., recovering the olefin-free diluent using the heavies column instead of the lights column), energy efficiency of the overall polymer production process can be improved by at least about 30% (e.g., energy consumption may be reduced by at least about 30%) in comparison to systems and processes which i) do not utilize a side rectifier column in combination with a heavies column and/or ii) recover the same components using the lights column. Olefin efficiency also can be improved according to the present disclosure.

Turning now to the figures, FIG. 1 illustrates a process flow diagram of an olefin and diluent recovery system 100 which utilizes a side rectifier column 130 in combination with a heavies column 110 to recover olefin-free diluent from a feed stream containing olefin and diluent. The system 100 also can include a lights column system 120 (e.g., including a main column 122 and a vent column 126) located downstream of the heavies column 110. Within the scope of the system 100 of FIG. 1, it is contemplated that various equipment associated with olefin and diluent recovery systems (e.g., valves, pumps, accumulators, piping, reboilers, condensers, heaters, compressors, control systems, safety equipment, and the like), while not shown for purposes of clarity, can be included in the system 100 according to techniques known in the art with the aid of this disclosure. As used herein, the term "diluent" shall mean compounds or materials capable of functioning as a solvent for the components of a polymerization process of the present invention, wherein the compounds or materials do not react to any substantial degree with the monomers used or polymer formed during the polymerization process. Preferably, diluents of the present invention act as a solvent for both the monomers and for the polymer produced. The term "monomer" shall mean an olefin which can be polymerized in the presence of a polymerization catalyst. The term "comonomer" shall mean another olefin (different than the monomer) which can be polymerized in addition to the monomer. In a specific aspect, the diluent can be isobutane, the monomer can be ethylene, and the comonomer is 1-hexene, with the understanding that any suitable combination of inert diluent (such as isobutane or isopentane), monomer, comonomer, etc. may be employed as would be understood to those skilled in the art.

In the system 100 of FIG. 1, a feed stream 112 containing components from a polymerization process (e.g., remaining portions of a polymerization reactor effluent following removal of polymer solids) can feed to, or is introduced to, the heavies column 110. The feed stream 112 can contain components from the upstream polymerization process, e.g., isobutane, 1-hexene, hexane, oligomers, and optionally one or more of hydrogen, ethane, nitrogen, and ethylene in varying amounts. Additionally, the feed stream 112 can contain fresh comonomer (e.g., fresh 1-hexene), fresh diluent (e.g., fresh isobutane), or both fresh comonomer and fresh diluent (e.g., both fresh 1-hexene and fresh isobutane). The components can be fed in a liquid phase, vapor phase, or combination of liquid and vapor phases to the heavies column 110 via feed stream 112. The components of feed stream 112 can be obtained from polyolefin recovery equipment (e.g., a flash tank and/or a degassing vessel), an isobutane and nitrogen recovery unit (INRU), a fresh comonomer source, a fresh diluent source, or a combination thereof. It is contemplated that, in accordance with at least one aspect of the present disclosure, feed stream 112 may be a combination of streams from the various component sources described above, e.g., a combination of streams selected from a flash tank overhead (the gases recovered from a flash tank), a degassing vessel overhead (the gases recovered from a degassing vessel), an INRU liquids stream, a fresh comonomer source, and a fresh diluent source. Alternatively, the feed stream 112 can include multiple streams that feed separately to the heavies column 110. For example, feed stream 112 can include i) a first stream which feeds components from a flash tank overhead, and/or a degassing vessel overhead, and/or an INRU liquids stream, or a combination thereof to the heavies column 110, ii) a second stream which feeds fresh comonomer to the heavies column 110 separately of the first stream, and iii) a third stream which feeds fresh diluent to the heavies column 110 separately of the first stream and the second stream.

The components in feed stream 112 can be compressed (e.g., via a compressor, not shown) to an elevated pressure prior to their introduction into the heavies column 110 such that one or more components of the feed stream 112 are in a gas phase, a liquid phase, or both. Feed stream 112 can feed to any location of the heavies column 110, for example, to a bottom stage 206, to an intermediate stage 204, or to a stage 202 of the heavies column 110 above the intermediate stage 204. In accordance with an aspect of the present disclosure, and as illustrated in FIG. 1, the feed stream 112 can feed to an intermediate stage 204, for example a stage located below the top ¼ of the column height and above the bottom ¼ of column height (e.g., a middle half of the column), alternatively at stage located below the top ⅓ of the column height and above the bottom ⅓ of column height (e.g., a middle third of the column).

The heavies column 110 can operate at conditions to separate, via fractionation techniques known in the art with the aid of this disclosure, the feed stream 112 into an overhead stream 114 (e.g., which includes isobutane and light gases associated with polymerization processes such as one or more of hydrogen, ethane, nitrogen, and ethylene; i.e., components lighter (a smaller molecular weight or less dense) than 1-hexene), a side-draw stream 116 (e.g., which includes recycle-grade 1-hexene), and a heavies purge bottoms stream 118 (e.g., which include purge heavies such as hexane and oligomers, i.e., components heavier than 1-hexene). One or more components in overhead stream 114 can be characterized as vaporized solvents, diluent, unreacted olefin monomer and/or optional unreacted olefin comonomer, waste gases (e.g., secondary reaction products, such as contaminants and the like). The overhead stream 114 can further include oxygen, methane, propylene, propane, butane, 1-butene, isobutane, pentane, other light gases known in the art with the aid of this disclosure, or combinations thereof. For example, isobutane, ethylene, and light gases can be recovered in the overhead stream 114 from the heavies column 110.

The overhead stream 114 can enter a condenser 150 where the overhead stream 114 can be condensed to yield a gas phase and a liquid phase in stream 151. Gaseous phase and liquid phase components in stream 151 can then enter an accumulator 152 where the gaseous and liquid components can be separated into a vapor phase of gaseous components (e.g., ethylene and light gases) in stream 153 and a liquid phase (e.g., isobutane and heavier components) in stream 155. The liquid phase in stream 155 can be pumped via pump 156 to recycle isobutane and any components heavier than isobutane (e.g., 1-hexene and heavier) in stream 157 back to heavies column 110, to a stage at, near, or proximate the top 117 of the heavies column 110.

The uncondensed gaseous components (e.g., ethylene, light gases, any uncondensed isobutane), also referred to herein as the first portion of the overhead stream 114, recovered in the accumulator 152 can flow via stream 153 to the lights column system 120. The stream 153 flowing from the accumulator 152 can include a compressor 154. The compressor 154 can compress the components in the stream 153 to a pressure of about 220 psig (1,516.8 kPag) to about 320 psig (2,206.3 kPag). Alternatively, the stream 153 may not have a compressor 154.

As discussed above, the liquid phase of diluent, also referred to herein as the second portion of the overhead stream 114, can flow in stream 155 from the accumulator 152 to pump 156. A part of the second portion can be pumped in stream 159 to a heat exchanger 170 for preheating before being introduced to the lights column system 120 via stream 171. Heat in the heat exchanger 170 can be provided via steam or with the bottoms stream 128 of the lights column system 120. Preheating the liquid phase in stream 159 can help with ethane rejection from the recycle grade isobutane separated in the lights column system 120.

The side-draw stream 116 can be recovered from the heavies column 110. The side-draw stream 116 recycles 1-hexene to processing equipment (e.g., for purification) or directly to a polymerization reactor. The side-draw stream 116 can recover comonomer at a bottom stage 206 (referred to herein as a "recycle hexene takeoff stage") of the heavies column 110 which can be located below the side rectifier column 130.

The heavies purge bottoms stream 118 can also be recovered from the heavies column 110. The purge heavies can flow via heavies purge bottoms stream 118 for further processing and/or use. A portion of the purge heavies can flow from the heavies column 110 in stream 113 to a reboiler 111 and return to the bottom 119 of the heavies column 110 via reboiler stream 115. Alternatively, the purge heaves flow in bottoms stream 118 without being reboiled.

With continued reference to FIG. 1, the heavies column 110 can operate at a pressure of about 100 psig (689.5 kPag) to about 250 psig (1,723.7 kPag). The heavies column 110 can operate at an overhead temperature of about 100° F. (37.8° C.) to about 200° F. (93.3° C.), and at a bottoms temperature of about 300° F. (148.9° C.) to about 400° F. (204.4° C.).

The heavies column 110 can be a vessel having internal components such as a plurality of distillation trays (e.g., sieve-type, dual-flow, bubble cap, donut, or a combination thereof), packing materials, or both. In an aspect, the heavies column 110 can be a distillation or fractionation column. At least one distillation tray can correspond to a stage in the heavies column 110. That is, in accordance with aspects of the present disclosure, a single stage in the heavies column 110 can include one or more distillation trays.

The side-rectifier column 130 receives isobutane and 1-hexene from an intermediate stage 204 of the heavies column 110. Olefin-free diluent, e.g., olefin-free isobutane, can be recovered from the side rectifier column 130. The side rectifier column 130 can be positioned internally or externally of the heavies column 110. Appropriate techniques can be used for securing the side rectifier column 130 internally or externally of the heavies column 110. FIG. 1 illustrates that the side rectifier column 130 can be positioned internally within the heavies column 110.

The term "side" when used with "rectifier column" herein is intended to mean that the operation of the side rectifier column 130 can be dependent upon the operation of the heavies column 110. For example, the side rectifier column 130 can recover olefin-free diluent by receiving isobutane and 1-hexene vapors from a stage 204 of the heavies column 110 (referred to herein as an "intermediate stage") which can be between the stage 202 where feed stream 112 feeds to the heavies column 110 (referred to herein as a "feed stage") and the stage 206 where the side-draw stream 116 flows from the heavies column 110 (referred to herein as a "recycle hexene takeoff stage"). The bottom 133 of the side rectifier column 130 generally can be positioned above the recycle hexene takeoff stage 206 of the heavies column 110. As an example of operation, isobutane and 1-hexene vapors can flow into the side rectifier column 130 directly through an opening in the bottom 133 (e.g., when internally positioned) or via vapor gathering/directing internals or piping or other conduit (e.g., for an externally positioned side rectifier column). In an additional or alternative example of operation which depends on the heavies column 110, the side rectifier column 130 operates using heat supplied by the reboiler of the heavies column 110.

Figure 3:
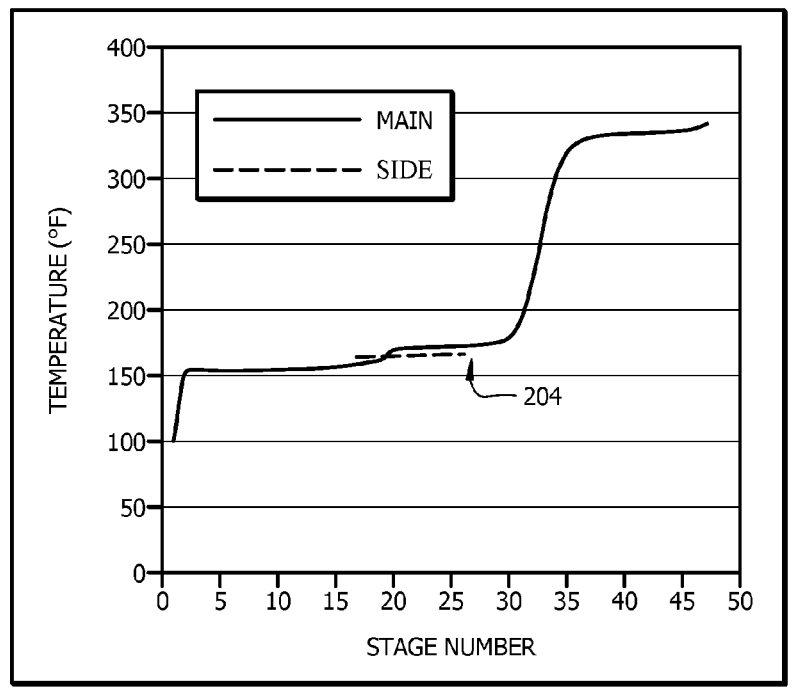
FIG. 3 is a graph of temperature versus stage number for a heavies column and a side rectifier column in Example 1.

The side rectifier column 130 can operate at a pressure of about 100 psig (689.5 kPag) to about 250 psig (1,723.7 kPag). The side rectifier column 130 can operate at an overhead temperature of about 100° F. (37.8° C.) to about 200° F. (93.3° C.), and at a bottoms temperature of about 100° F. (37.8° C.) to about 200° F. (93.3° C.). In accordance with an aspect of the present invention, the side rectifier column 130 can have about a uniform temperature from the top 131 to the bottom 133, for example, a temperature of about 160° F. (65.6° C.) as illustrated in FIG. 3 and described in more detail in Example 1. The temperature of specific stages of the side rectifier column 130 relative to stages of the heavies column 110 is discussed in more detail below.

The side rectifier column 130 can be a vessel having internal components such as a plurality of distillation trays (e.g., sieve-type, dual-flow, bubble cap, donut, or a combination thereof), packing materials, or both. For example, the side rectifier column 130 can be a distillation or fractionation column. At least one distillation tray can correspond to a stage in the side rectifier column 130. That is, a single stage in the side rectifier column 130 can include one or more distillation trays.

The side rectifier column 130 can have a diameter smaller than a diameter of the heavies column 110. The number of stages in the side rectifier column 130 generally can be fewer than the number of stages in the heavies column 110.

The intermediate stage 204 of the heavies column 110 can be a stage in which the vapor phase has less than 1 parts per million by weight ("ppmw") ethylene. For example, in a heavies column 110 which has 47 stages (numbered 1 to 47 from top 117 to bottom 119 of the heavies column 110), stages 23 to 47 of the heavies column 110 can have ethylene concentrations less than 1 ppmw in the vapor phase, and the intermediate stage 204 can be any of stages 23 to 47 which contains vapor phase. Vapors from below the intermediate stage 204 of the heavies column 110 can flow into the bottom 133 of the side rectifier column 130. The vapors can rise through the stages (e.g., 11 stages, from stage 11 to stage 1) inside the side rectifier column 130 from bottom 133 to top 131. As the vapors rise, the concentration of 1-hexene can be reduced below a threshold level such that isobutane withdrawn from the side rectifier column 130 in stream 132 can be suitable for contact with polymerization catalyst (e.g., substantially olefin-free diluent) as disclosed in more detail herein. 1-hexene condenses and falls downwardly in the side rectifier column 130, thereby exiting the bottom 133 of the side rectifier column 130 and flowing back into the heavies column 110.

It is contemplated that one or more conditions of a particular stage in the side rectifier column 130 can be similar to a corresponding particular stage of the heavies column 110. The term "corresponding stages", as used herein, means a pair of stages (e.g., one stage from the heavies column 110 and one stage from the side rectifier column 130) which have similar operating conditions. For example, and without limitation, the side rectifier column 130 can have 11 stages (numbered 1 to 11 from top 131 to bottom 133 of the side rectifier column 130), the heavies column 110 can have 47 stages (numbered 1 to 47 from top 117 to bottom 119 of the heavies column 110), and stage number 27 of the heavies column 110 can be the intermediate stage 204 where vapors from the heavies column 110 flow into stage number 11 of the side rectifier column 130 (see, e.g., FIG. 3). Vapors which enter the side rectifier column 130 at stage 11 (near the bottom 133) can rise up through stages 11, 10, 9, 8, 7, 6, 5, 4, 3, 2, and 1. Thus, stages 1 to 11 of the side rectifier column 130 can operate at similar conditions as, i.e., correspond to, stages 17 to 27 of the heavies column 110. In such an example, each pair of stages (stage 1 of the side rectifier column 130 and stage 17 of the heavies column 110, stage 2 of the side rectifier column 130 and stage 18 of the heavies column 110, and so on) can operate at similar temperatures (e.g., ±1, 2, 3, 4, 5, or 6° F. (±0.5, 1.1, 1.7, 2.2, 2.8, or 3.3° C.) of each other) and/or pressures (e.g., ±1, 2, 3, 4, 5, or 6 psig (6.9, 13.8, 20.7, 27.6, 34.4, or 41.4 kPag) of each other). For example, a given stage of the side rectifier column 130 can have a temperature about 4° F. (2.2° C.) to about 6° F. (3.3° C.) different (hotter or cooler) than the corresponding given stage of the heavies column 110. The discussion of relative temperatures between the side rectifier column 130 and heavies column 110 continues in the description for Example 1 below.

Continuing to refer to the process illustrated in FIG. 1, the olefin-free isobutane stream 132 containing 1-hexene below the threshold level can flow from the side rectifier column 130. The olefin-free isobutane stream 132 can flow from a top 131 of the side rectifier column 130. When the side rectifier column 130 is positioned internally of the heavies column 110, appropriate piping or other structure can be connected to the side rectifier column 130 and extends through the interior 208 and also externally of the heavies column 110 (e.g., through a sidewall of the heavies column 110) so that components in the olefin-free isobutane stream 132 do not escape to the interior 208 of the heavies column 110 while flowing from the side rectifier column 130. In aspects where the side rectifier column 130 is positioned externally of the heavies column 110, piping can be connected to the side rectifier column 130 without concern that components of the olefin-free isobutane stream 132 can escape to the interior 208 of the heavies column 110.

When the side rectifier column 130 is positioned external to the heavies column 110, appropriately located piping may connect the bottom 133 of the side rectifier column 130 with the interior 208 of the heavies column 110 such that vapors from below the intermediate stage 204 of the heavies column 110 flow into the bottom 133 of the side rectifier column 130 via the piping. After separation from isobutane in the side rectifier column 130, 1-hexene can return back in to the interior 208 of the heavies column 110 via the appropriately located piping.

The olefin-free isobutane stream 132 flows to a condenser 160 where components are condensed. The olefin-free isobutane flows from the condenser 160 in stream 161 to a collection tank 162. The olefin-free isobutane flows from the collection tank 162 in stream 163 to a pump 164. The pump 164 can recycle a first portion of the olefin-free isobutane in stream 167 to a stage at or near the top 131 of the side rectifier column 130 and below the location where the olefin-free isobutane stream 132 removes components from the side rectifier column 130. The pump 164 can also recycle a second portion of the olefin-free isobutane in stream 165 for use as diluent in the polymerization process or storage for a later use.

The olefin-free isobutane stream (including reflux stream 167 and recycle stream 165 described herein) includes isobutane and can be substantially olefin-free. As used herein, "substantially olefin-free" means less than about 0.1, 0.09, 0.08, 0.07, 0.06, 0.05, 0.04, 0.03, 0.02, 0.01 wt. % olefin by weight of the olefin-free isobutane stream 132 (and any portion of the olefin-free isobutane stream 132). The olefin-free isobutane stream 132 can include less than 1,000 ppmw 1-hexene based on a total weight of the olefin-free isobutane stream 132 (and any portion of the olefin-free isobutane stream 132). The olefin-free isobutane stream 132 can also include less than 1 ppmw ethylene based on a total weight of the olefin-free isobutane stream 132.

The lights column system 120 operates at conditions which separate the components received in stream 171 to recover ethylene and other light gases in one stream and to recover isobutane in another stream. FIG. 1 generally illustrates the lights column system 120 comprising, or including, two columns, a main column 122 and a vent column 126; however, the disclosure contemplates that the lights column system 120 can be a single column having an overhead stream and a bottoms stream. The lights column system 120 can be a "system" of one or more vessels having internal components such as a plurality of distillation trays (e.g., sieve-type, dual-flow, bubble cap, donut, or a combination thereof), packing materials, or both. For example, one or more of the main column 122 and vent column 126 in FIG. 1 can be a distillation or fractionation column. At least one distillation tray can correspond to a stage in the lights column system 120. That is, a single stage in the lights column system 120 can include one or more distillation trays.

In FIG. 1, stream 171 can enter the main column 122 and can be separated into overhead stream 124 and bottoms stream 128 of the main column 122. The overhead stream 124 of the main column 122 can flow to the vent column 126. Bottoms product can be recovered from the bottom 226 of the vent column 126 in stream 129. Pump 180 can be used to recycle the bottoms product to the top 222 of the main column 122 as reflux in stream 181.

Generally, an overhead stream can be recovered from the lights column system 120. In FIG. 1, the overhead stream which is recovered can be stream 127 of the vent column 126. One or more of the light gases can flow via overhead stream 127 for further processing and/or use. For example, the components of overhead stream 127 can flow to an ethylene recovery unit where any ethylene contained in stream 127 is separated from other light components. Light gases which are not recovered for use in subsequent processes can be considered fuel or waste gases and dealt with accordingly. Volatile components (e.g., one or more gases described as light gases herein) introduced into the system 100 by fresh comonomer, fresh diluent, or both fresh comonomer and fresh diluent also can be recovered in the overhead stream 127.

Generally, a bottoms stream can be recovered from the lights column system 120. In FIG. 1, isobutane and optionally ethylene can be recovered in the bottoms stream 128 of the main column 122. Isobutane can flow via bottoms stream 128 or stream 173 for further processing and/or recycle to a polymerization process. A portion of the isobutane can flow from the main column 122 in stream 123 to a reboiler 121 and can return to the bottom 224 of the main column 122 via stream 125. Alternatively, no reboiler is utilized.

The lights column system 120 (e.g., one or more of the main column 122 and the vent column 126) can operate such that the bottoms stream 128 also contains ethylene which would otherwise be lost in the overhead stream 127. Accordingly, the isobutane in the bottoms stream 128 can be "not substantially olefin-free", meaning that bottoms stream 128 can comprise greater than about 0.01, 0.02, 0.03, 0.04, 0.05, 0.06, 0.07, 0.08, 0.09, 0.1 wt. % olefin by weight of the bottoms stream 128. The bottoms stream 128 can include greater than 1,000 ppmw 1-hexene based on a total weight of the bottoms stream 128. The bottoms stream 128 can include greater than 1 ppmw ethylene based on a total weight of the bottoms stream 128. The lights column system 120 (e.g., one or more of the main column 122 and the vent column 126) can operate such that less than 1 ppm hydrogen is present in the bottoms stream 128 based on a total moles of components in the bottoms stream 128. The amount of hydrogen in the bottoms stream 128 can be measured by taking a sample and analyzing such according to methods known in the art.

The lights column system 120 described herein can operate such that olefin-free isobutane can be recovered only from the side rectifier column 130 and not in the lights column system 120. The lights column system 120 (e.g., one or more of the main column 122 and the vent column 126) may have no side draw stream.

The lights column system 120 (e.g., one or more of the main column 122 and vent column 126) can operate at a pressure or with a range of pressures of about 150 psig (1,034.2 kPag) to about 350 psig (2,413.2 kPag). The lights column system 120 can operate at an overhead temperature of about −20° F. (−28.9° C.) to about 105° F. (40.6° C.) and at a bottoms temperature of about 66° F. (18.9° C.) to about 250° F. (121.1° C.). Alternatively, the lights column system 120 can operate at an overhead temperature of about −10° F. (−23.3° C.) to about 100° F. (37.8° C.), and at a bottoms temperature of about 66° F. (18.9° C.) to about 250° F. (121.1° C.

The vent column 126 can generally operate at a temperature and pressure lower than the main column 122. For example, the vent column 126 can operate in a range of temperatures from about −20° F. (−28.9° C.) to about 150° F. (65.6° C.) and a range of pressures from about 319 psig (2,199.4 kPag) to about 320 psig (2,206.3 kPag); while the main column 122 can operate in a range of temperatures from about 150° F. (65.6° C.) to about 200° F. (93.3° C.) and a range of pressures from about 320 psig (2,206.3 kPag) to about 325 psig (2,240.8 kPag).

The pressure of the lights column system 120 (e.g., of one or more of the main column 122 and vent column 126) can be greater than a pressure of the heavies column 110. For example, the lights column system 120 (e.g., one or more of the main column 122 and vent column 126) can operate at one or more pressures in a range of about 150 psig (1,034.2 kPag) to about 350 psig (2,413.2 kPag) while the heavies column 110 can operate at one or more pressures in a range of 100 psig (689.5 kPag) to about 250 psig (1,723.7 kPag), with at least one pressure of the lights column system 120 being greater than at least one pressure of the heavies column 110.

Without being limited by theory, it is thought that operating the lights column system 120 at a higher pressure can reduce olefin(s) (e.g., ethylene, 1-hexene, or both) and diluent (e.g., isobutane) losses experienced when operating the lights column system 120 at temperatures available when utilizing traditional cooling water systems or propane/propylene refrigerant systems.

Figure 2:
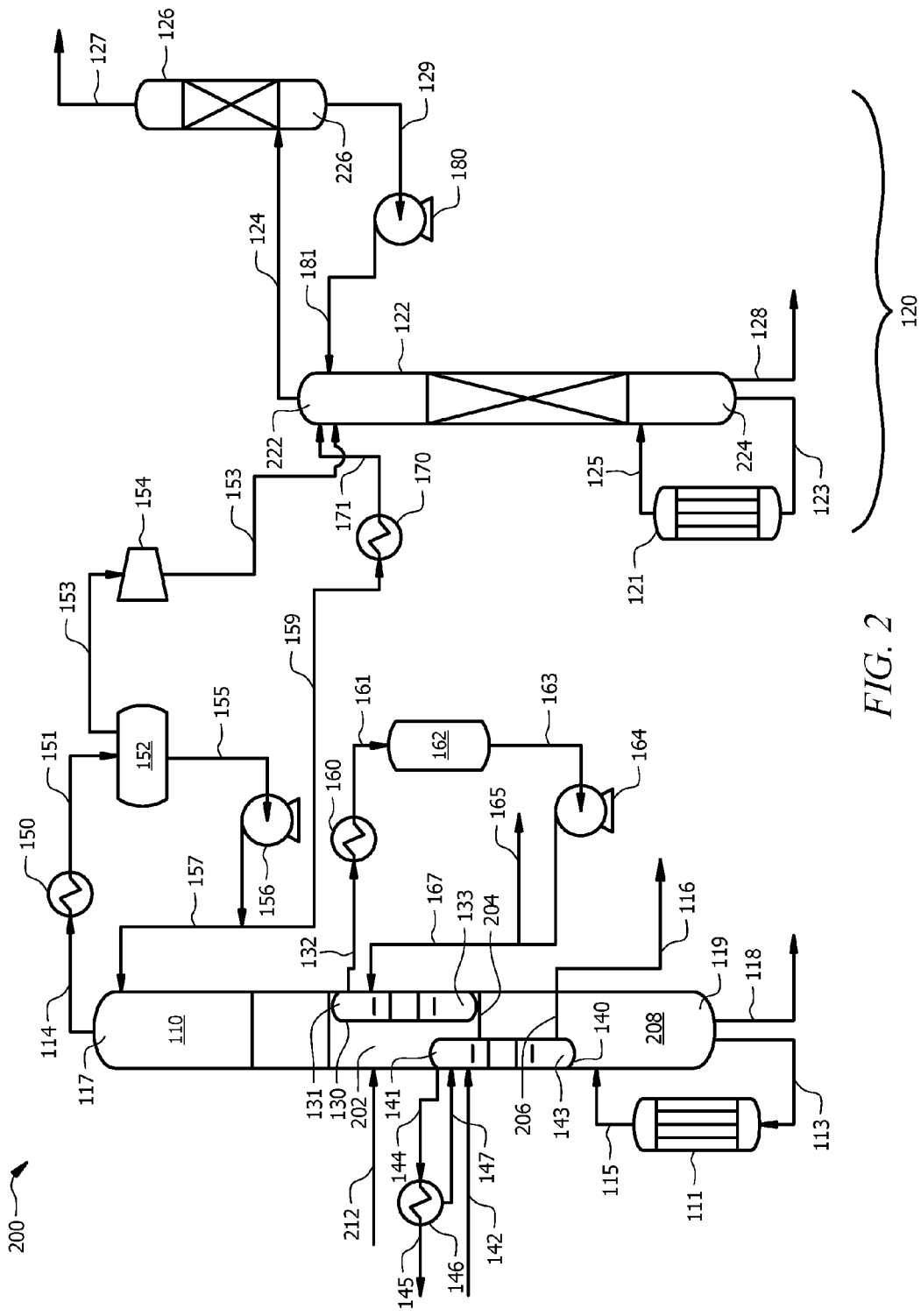
FIG. 2 illustrates an exemplary process flow diagram of an olefin and diluent recovery system similar to that presented in FIG. 1, utilizing a side rectifier column and a side degassing column in combination with a heavies column to recover light gases.

FIG. 2 illustrates a process flow diagram of an olefin and diluent recovery system 200. The system 200 of FIG. 2 can include a heavies column 110, a lights column system 120, a side rectifier column 130, and a side degassing column 140. Within the scope of the system 200 of FIG. 2, it is contemplated that various equipment associated with olefin and diluent recovery systems (e.g., valves, pumps, accumulators, piping, reboilers, condensers, heaters, compressors, control systems, safety equipment, and the like), while not shown for purposes of clarity, can be included in the system 200 according to techniques known in the art with the aid of this disclosure.

The feed stream 212 containing components recovered from a polymerization process (e.g., remaining portions of a polymerization reactor effluent following removal of polymer solids, such as diluent, monomer, comonomer, and the like) can feed to the heavies column 110. The feed stream 212 differs from the feed stream 112 of FIG. 1 in that fresh components can be fed to the system 200 in fresh feed stream 142, and not feed stream 212. The operation of the heavies column 110 which receives the feed stream 212, the operation of the lights column system 120, and the operation of the side rectifier column 130 in FIG. 2 are similar to that described in FIG. 1, with certain distinguishing features described in more detail below after a discussion of the fresh feed stream 142 and side degassing column 140. To the extent distinguishing features are not discussed below with regard to a component of the system 200 in FIG. 2, it is contemplated that the operation can be the same as that described for the system 100 in FIG. 1 (e.g., the operation of the side rectifier column 130 in FIG. 2 can be the same as described for FIG. 1).

The fresh feed stream 142 can be used to feed fresh comonomer (e.g., fresh 1-hexene) and/or fresh diluent (e.g., fresh isobutane), and/or volatile components (e.g., one or more of the light gases described herein) to the side degassing column 140. The concentration of any inert components in fresh feed stream 142 (e.g., components which are inert in polymerization, such as isobutane and nitrogen) can be less than the concentration of comonomer. The concentration of monomer (e.g., 1-hexene) in the fresh feed stream 142 can be greater than 95 wt. %, 96 wt. %, 97 wt. %, 98 wt. %, or 99 wt. % based on a total weight of components in the fresh feed stream 142. The fresh feed stream 142 can include appropriate piping which can be connected to the top 141 (or alternatively, near the top 141) of the side degassing column 140 and can extend through the interior 208 and also externally of the heavies column 110 so that components in the fresh feed stream 142 do not escape to the interior 208 of the heavies column 110 while flowing to the side degassing column 140.

The side degassing column 140 can separate components of the fresh feed stream 142. For example, comonomer (e.g., 1-hexene) and/or diluent (e.g., isobutane) can be recovered in the side degassing column 140. The term "side" when used with "degassing column" herein is intended to mean that the operation of the side degassing column 140 can be dependent upon the operation of the heavies column 110. For example, the side degassing column 140 can operate using heat supplied by the reboiler 111 of the heavies column 110.

The side degassing column 140 can operate at a pressure of about 100 psig (689.5 kPag) to about 250 psig (1,723.7 kPag). The side degassing column 140 can operate at an overhead temperature of about 100° F. (37.8° C.) to about 200° F. (93.3° C.), and at a bottoms temperature of about 100° F. (37.8° C.) to about 400° F. (204.4° C.). In an aspect, the side degassing column 140 can have about a uniform temperature from the top 141 to the bottom 143.

The side degassing column 140 can be a vessel having internal components such as distillation trays (e.g., sieve-type, dual-flow, bubble cap, donut, or a combination thereof), packing materials, or both. For example, the side degassing column 140 can be a distillation or fractionation column. At least one distillation tray can correspond to a stage in the side degassing column 140. That is, a single stage in the side degassing column 140 can include one or more distillation trays.

The side degassing column 140 can be positioned internally of the heavies column 110, for example between the inlet of feed stream 212 and the inlet of reboiler stream 115. Instead of having a reboiler dedicated to the side degassing column 140, the internal positioning of the side degassing column 140 (e.g., above or proximate the entry point of reboiler stream 115) allows for use by the side degassing column 140 of heat in the heavies column 110 supplied by the reboiler of the heavies column 110. The side degassing column 140 can be positioned internally of the heavies column 110, and at least a part (e.g., the top 141) of the side degassing column 140 can be positioned between the feed stage 202 and the recycle hexene takeoff stage 206 of the heavies column 110.

Positioning the side degassing column 140 positioned internally of the heavies column 110 allows the side degassing column 140 to use the heat of the heavies column 110 to remove the volatile components which would otherwise be removed by the lights column system 120 in the absence of the side degassing column 140.

The side degassing column 140 can have a diameter smaller than a diameter of the heavies column 110. Additionally, the number of stages in the side degassing column 140 generally can be fewer than the number of stages in the heavies column 110.

In operation, the side degassing column 140 can receive fresh feed stream 142 and separates the components thereof. The flow rate of the fresh feed stream 142 can be relatively low compared to the flow of materials within the heavies column 110. In the side degassing column 140, the components of the fresh feed stream 142 can separate such that the volatile components fed to the side degassing column 140 can flow from the top 141 of the side degassing column 140 via overhead stream 144. Overhead stream 144 can be positioned above the feed stream 142. Heavier components in the side degassing column 140 can fall down the side degassing column 140, can flow from the bottom 143 of the side degassing column 140 (e.g., in a side degassing column bottoms stream), and can mix with the material in the heavies column 110 at or around the recycle hexene takeoff stage 206, or side-draw stream 116.

When fresh feed stream 142 contains fresh comonomer and no diluent, the fresh comonomer can fall downward through the side degassing column 140 and can flow from a bottom 143 of the side degassing column 140 into the heavies column 110.

When fresh feed stream 142 contains fresh diluent and no comonomer, the fresh diluent can fall downward through the side degassing column 140 such that the fresh diluent can be concentrated (e.g., a location near the inlet of the fresh feed stream 142) and into the heavies column 110. In an aspect, the location where the fresh diluent is concentrated can be at a stage of the side degassing column 140 which is near and below the location where the fresh feed stream 142 enters the side degassing column 140.

When fresh feed stream 142 includes both fresh diluent and fresh comonomer, the fresh comonomer and diluent can fall downward through the side degassing column 140 and can flow from the side degassing column 140 either in the same stage or in separate stages.

The overhead stream 144 generally can be fed back (e.g., as reflux) to a stage of the side degassing column 140 which is above the stage where fresh feed stream 142 is introduced. The overhead stream 144 of the side degassing column 140 can include a condenser 146 which condenses at least a portion of the overhead stream 144 (any components heavier than the volatile components, e.g., comonomer and/or diluent) for recycle to a stage at the top 141 of the side degassing column 140 in stream 147. Using the condenser 146, volatile components from overhead stream 144 can flow from the system in stream 145, and a liquid phase recovered from the overhead stream 144 can be recycled back to the side degassing column 140 as reflux in stream 147.

In some aspects, the side degassing column 140 may not receive vapors from the interior 208 of the heavies column 110 (e.g., the internal contents of the side degassing column 140 are isolated from the internal contents of the heavies column 110). That is, diluent and/or comonomer recovered from the side degassing column 140 can flow via a bottom stream (not shown) into the interior 208 of the heavies column 110 without vapor from the interior 208 of the heavies column 110 entering the side degassing column 140. In other aspects, the side degassing column 140 can receive vapors from the interior 208 of the heavies column 110, similar to the side rectifier column 130.

Features of the heavies column 110 and the lights column system 120 of the system 200 in FIG. 2 are now discussed. In the system 200 of FIG. 2, isobutane and 1-hexene can feed to the feed stage 202 of the heavies column 110 in feed stream 112 separate of any fresh comonomer and/or fresh diluent fed to the side degassing column 140 in stream 142.

In the system 200 of FIG. 2, the condenser 150 can be used to condense at least a portion of the overhead stream 114 to yield different components in stream 151 of FIG. 2 in comparison to stream 151 in FIG. 1. For example, a vapor phase of gaseous components (e.g., hydrogen) and a liquid phase of diluent (e.g., isobutane) and optionally unreacted monomer (e.g., ethylene) can flow in stream 151 of FIG. 2. FIG. 2 also shows bottoms stream 128 of the lights column system 120 may not be used to cross-exchange heat with stream 159. However, it is contemplated that the configuration of stream 128 in system 200 of FIG. 2 (e.g., no heat cross-exchange) can be utilized in the system 100 of FIG. 1, and likewise the configuration of stream 128 in system 100 of FIG. 1 (e.g., heat cross-exchange) can be utilized in the system 200 of FIG. 2. Stream 151 can flow to accumulator 152 to produce gaseous stream 153 and liquid stream 155 that may be further processed as discussed with reference to FIG. 1. For example, the lights column system 120 may produce gaseous components (e.g., hydrogen from the vapor phase) in the overhead stream 127 and a reduced-hydrogen liquid phase in the bottoms stream 128 of the lights column system 120. In an aspect, the reduced-hydrogen liquid phase recycled to the polymerization process in stream 128 is not olefin-free diluent, e.g., is not olefin-free isobutane.

Shifting recovery of olefin-free isobutane away from the lights column system 120 according to the disclosed systems and processes can reduce energy consumption by at least about 30% in comparison to otherwise similar olefin and diluent recovery systems and processes which do not utilize the side rectifier column in combination with the heavies column 110. While not intending to be limited by theory, it is thought that shifting recovery of olefin-free isobutane from the lights column system 120 reduces energy consumption because the olefin-free diluent recovery disclosed herein is about 2% to about 3% of the total diluent flow in the disclosed systems and processes, compared with about 50% of the total diluent flow in otherwise similar olefin and diluent recovery processes and systems which do not utilize the side rectifier column 130 in combination with the heavies column 110.

Energy consumption can be measured as the amount of energy input into an olefin polymerization reactor process/system (which includes the olefin and diluent recovery process/system) divided by the amount of polyolefin produced, in units of [kWh/kg] or [Btu/lb]. Alternatively, energy consumption can be measured as the amount of energy input into an olefin and diluent recovery system or process divided by the amount of olefin (e.g., monomer, comonomer, or both monomer and comonomer) and/or diluent (e.g., isobutane) recovered by said olefin and diluent recovery system or process, in units of [kWh/kg] or [Btu/lb].

Energy input into the respective process/system can be in any form, e.g., electricity, steam, and/or fuel gas. Similar energy consumption calculations in the context of polyolefin production can be found in U.S. Pat. Nos. 8,128,877, 8,017, 701, 8,303,899, 8,569,433, 8,765,884, and 9,221,920; and European Patent No. 1791875B1, each of which is incorporated by reference in its entirety.

The systems and processes disclosed herein can improve olefin efficiency. "Olefin efficiency" as used herein relates to the efficiency of producing polyolefin in a polymerization process and is defined as the ratio of pounds of olefin fed to a polymerization process to pounds of polyolefin produced in the polymerization process. A value of 1.0 means that all the olefins supplied to the polymerization process are reacted in the polymerization process to form a polyolefin. A value greater than 1.0 means, pound for pound, more olefins are supplied to the polymerization process than are converted to polyolefin. Without being limited by theory, it is thought that olefin efficiency is improved because olefin-free diluent is recovered upstream of the lights column system 120, and the lights column system 120 only recovers recycle-grade isobutane (which can contain ethylene). Since the disclosed lights column system 120 does not recover olefin-free diluent, the ethylene which travels through the olefin and diluent recovery systems 100 and 200 disclosed herein can be recovered with the diluent (e.g., isobutane) in the bottoms stream 128 of the lights column system 120 and is not lost to possible waste in the overhead stream 127 of the lights column system 120. Some ethylene can be lost in the overhead stream 127 of the lights column system 120 (e.g., when the overhead stream 127 does not flow to an ethylene recovery unit); however, olefin efficiency is still improved because the ethylene lost is less than the ethylene lost in systems and processes which recover olefin-free isobutane in the lights column system 120. Less ethylene is lost because the lights column system 120 disclosed herein can operate at conditions which allow ethylene and isobutane to flow in the bottoms stream 128 of the lights column system 120 for recycle to the polymerization process.

The systems and processes disclosed herein can provide an olefin efficiency of less than about 1.010. For example, in polymerization processes utilizing Ziegler-Natta catalyst systems to produce bimodal resins, olefin efficiency using the disclosed systems and processes can be less than about 1.010. For polymerization processes utilizing chromium catalyst systems and/or metallocene catalyst systems, olefin efficiency can be less than about 1.010 and as low as about 1.005.

The disclosed systems and processes also allow for a smaller lights column, which saves on capital and operating cost for the lights column system 120. Also, control of the lights column system 120 can be simplified since there is no need to control a side-draw stream. Moreover, the side rectifier column 130 and side degassing column 140 can shift recovery of olefin-free diluent and volatile components away from the lights column system 120 utilizing relatively small vessels. Thus, capital and operating expenditures for the side rectifier column 130 and side degassing column 140 are relatively small.

EXAMPLES

The subject matter having been generally described, the following examples are given as particular embodiments of the disclosure and are included to demonstrate the practice and advantages thereof, as well as preferred aspects and features of the inventions. It should be appreciated by those of skill in the art that the techniques disclosed in the examples which follow represent techniques discovered by the inventors to function well in the practice of the inventions, and thus can be considered to constitute preferred modes for its practice. However, those of skill in the art should, in light of the present disclosure, appreciate that many changes can be made in the specific aspects which are disclosed and still obtain a like or similar result without departing from the scope of the inventions of the instant disclosure. It is understood that the examples are given by way of illustration and are not intended to limit the specification of the claims to follow in any manner.

In Example 1, a system having a side rectifier column similar to the configuration shown in FIG. 1 is utilized. In Example 1, the diluent recovered is isobutane and the comonomer recovered is 1-hexene. Data regarding temperature, pressure, liquid flow rate, vapor flow rate, net feed rate, net draw rate, and duty for the stages in each of the heavies column, side rectifier column, and lights column was modeled using commercially available process modelling software such as Aspen. The data is reproduced below in Tables 1 to 4.

Table 1 below shows the operating conditions for the heavies column:

TABLE 1

Operating Conditions for Heavies Column in Example 1

| Stage (#) | Temperature (° F.) | Pressure (psig) | Net Feed (lbmol/hr) | Net Draw (lbmol/hr) | Duty (Btu/hr) |
|---|---|---|---|---|---|
| 1 | 100.0 | 150.0 | — | 2,052.9 | 21,822,863 |
| 2 | 152.0 | 150.0 | — | — | — |
| 3 | 153.9 | 150.1 | — | — | — |
| 4 | 154.1 | 150.2 | — | — | — |
| 5 | 154.2 | 150.3 | — | — | — |
| 6 | 154.3 | 150.5 | — | — | — |
| 7 | 154.3 | 150.6 | — | — | — |
| 8 | 154.4 | 150.7 | — | — | — |
| 9 | 154.5 | 150.8 | — | — | — |
| 10 | 154.7 | 150.9 | — | — | — |
| 11 | 154.9 | 151.0 | — | — | — |
| 12 | 155.1 | 151.1 | — | — | — |
| 13 | 155.5 | 151.3 | — | — | — |
| 14 | 156.0 | 151.4 | — | — | — |
| 15 | 156.7 | 151.5 | — | — | — |
| 16 | 157.7 | 151.6 | — | — | — |
| 17 | 159.0 | 151.7 | — | — | — |
| 18 | 160.7 | 151.8 | — | — | — |
| 19 | 162.8 | 151.9 | 2,125.2 | — | — |
| 20 | 169.7 | 152.0 | — | — | — |
| 21 | 171.1 | 152.2 | — | — | — |
| 22 | 171.5 | 152.3 | — | — | — |
| 23 | 171.8 | 152.4 | — | — | — |
| 24 | 172.0 | 152.5 | — | — | — |
| 25 | 172.3 | 152.6 | — | — | — |
| 26 | 172.7 | 152.7 | — | — | — |
| 27 | 173.1 | 152.8 | — | 33.1 | — |
| 28 | 173.7 | 153.0 | 15.9 | — | — |
| 29 | 175.1 | 153.1 | — | — | — |
| 30 | 179.1 | 153.2 | — | — | — |
| 31 | 191.4 | 153.3 | — | — | — |
| 32 | 221.2 | 153.4 | — | — | — |
| 33 | 264.9 | 153.5 | — | — | — |
| 34 | 300.3 | 153.6 | — | — | — |
| 35 | 319.3 | 153.8 | — | — | — |
| 36 | 327.8 | 153.9 | — | 52.8 | — |
| 37 | 331.5 | 154.0 | — | — | — |
| 38 | 333.1 | 154.1 | — | — | — |
| 39 | 333.9 | 154.2 | — | — | — |
| 40 | 334.5 | 154.3 | — | — | — |
| 41 | 334.9 | 154.4 | — | — | — |
| 42 | 335.4 | 154.5 | — | — | — |
| 43 | 335.8 | 154.7 | — | — | — |
| 44 | 336.2 | 154.8 | — | — | — |

TABLE 1-continued

Operating Conditions for Heavies Column in Example 1

| Stage (#) | Temperature (° F.) | Pressure (psig) | Net Feed (lbmol/hr) | Net Draw (lbmol/hr) | Duty (Btu/hr) |
|---|---|---|---|---|---|
| 45 | 336.7 | 154.9 | — | — | — |
| 46 | 337.3 | 155.0 | — | — | — |
| 47 | 341.1 | 155.0 | — | 2.3 | 5,556,061 |

In Table 1, stage 1 is the condenser (150) of the heavies column overhead stream (114), and has a liquid flow rate of 648.1 lbmol/hr (293.97 kgmol/hr) with no vapor flow. Stage 47 is the reboiler (111) for the heavies column bottoms stream (113), and has a vapor flow rate of 638.5 lbmol/hr (289.62 kgmol/hr) with no liquid flow. Thus, the heavies column (110) of Example 1 has 45 internal stages (stages 2 to 46 in Table 1).

As can be seen from the data in Table 1, the stages of the heavies column, i.e., stages 2 to 46, operate at a temperature of from 152.0° F. (66.7° C.) to 337.3° F. (169.6° C.) and a pressure of from 150.0 psig (1,034 kPag) to 155.0 psig (1,068.7 kPag). The condenser (150) operates at a temperature of 100.0° F. (37.8° C.) and a pressure of 150.0 psig (1,034 kPag). The reboiler (111) operates at a temperature of 341.1° F. (171.7° C.) and 155.0 psig (1,068.7 kPag).

Components to be recovered feed to the heavies column at stage 19 of the heavies column at a rate of 2,152.2 lbmol/hr (976.22 kgmol/hr).

The draw flow rate at stage 27 of 33.1 lbmol/hr (15.01 kgmol/hr) is the flow rate of isobutane and 1-hexene vapors into the side rectifier column (130) (compare the same value for feed flow into stage 11 of the side rectifier column (130) in Table 2, which provides mass balance). The feed flow rate at stage 28 of 15.9 lbmol/hr (7.21 kgmol/hr) is the flow of 1-hexene from the bottom (133) of the side rectifier column (130) back into the interior (208) of the heavies column (110) (again compare the same value for draw flow rate from stage 11 of the side rectifier column (130) in Table 2).

The draw flow rate of 52.8 lbmol/hr (23.95 kgmol/hr) at stage 36 of the heavies column (110) is the 1-hexene stream which is recycled to the polymerization process. The draw flow rate of 2052.9 lbmol/hr (931.18 kgmol/hr) is the flow rate of the overhead stream (114) of the heavies column (110) to the lights column system (120).

Table 2 below shows the operating conditions for the side rectifier column (130):

TABLE 2

Operating Conditions for Side Rectifier Column in Example 1

| Stage (#) | Temperature (° F.) | Pressure (psig) | Net Feed (lbmol/hr) | Net Draw (lbmol/hr) | Duty (Btu/hr) |
|---|---|---|---|---|---|
| 1 | 164.3 | 152.8 | — | 17.2 | 230,909 |
| 2 | 164.6 | 152.8 | — | — | — |
| 3 | 164.7 | 152.8 | — | — | — |
| 4 | 164.8 | 152.8 | — | — | — |
| 5 | 164.9 | 152.8 | — | — | — |
| 6 | 164.9 | 152.8 | — | — | — |
| 7 | 165.0 | 152.8 | — | — | — |
| 8 | 165.2 | 152.8 | — | — | — |
| 9 | 165.6 | 152.8 | — | — | — |
| 10 | 166.5 | 152.8 | — | — | — |
| 11 | 168.6 | 152.8 | 33.1 | 15.9 | — |

Stage 1 of the side rectifier column (130) is the condenser (160) in the olefin-free isobutane stream (132), and has a liquid flow rate of 17.2 lbmol/hr (7.80 kgmol/hr) liquid flowing at stage 1, with substantially no vapor flow. The side rectifier column (130) uses heat from the reboiler (111) of the heavies column (110) and has no reboiler itself. Thus, the side rectifier column (130) of Example 1 has 10 internal stages (stages 2 to 11 in Table 2).

As can be seen, the stages of the side rectifier column (130), i.e., stages 2 to 11, operate at a temperature of from 164.6° F. (73.7° C.) to 168.6° F. (75.9° C.) and a pressure of 152.8 psig (1,053.5 kPag) (constant pressure). The condenser (160) operates at a temperature of 164.3° F. (73.5° C.) and a pressure of 152.8 psig (1,053.5 kPag).

As seen in Table 2, vapor feeds from the heavies column (110) into the bottom (133) (at stage 11) of the side rectifier column (130) at a rate of 33.1 lbmol/hr (15.01 kgmol/hr) and exits the bottom (133) (stage 11) at a rate of 15.9 lbmol/hr (7.21 kgmol/hr). The vapor entering stage 11 is a mix of isobutane and 1-hexene. The vapor exiting stage 11 is primarily 1-hexene. Only vapor enters the side rectifier column (130), as indicated by no data in this simulation for liquid flow rate in Table 2. Olefin-free isobutane is recovered from the side rectifier column (130) at a rate of 17.2 lbmol/hr (7.80 kgmol/hr).

Table 3 below shows the corresponding stages for the heavies column (110) and the side rectifier column (130) of Example 1, along with the temperature difference of the corresponding stages.

TABLE 3

Corresponding Stages in Example 1 and Temperature Difference

| Side Rectifier Column Stage (#) | Heavies Column Stage (#) | Temperature Difference (° F.) |
|---|---|---|
| 2 | 18 | 3.9 |
| 3 | 19 | 1.9 |
| 4 | 20 | −4.9 |
| 5 | 21 | −6.2 |
| 6 | 22 | −6.6 |
| 7 | 23 | −6.8 |
| 8 | 24 | −6.8 |
| 9 | 25 | −6.7 |
| 10 | 26 | −6.2 |
| 11 | 27 | −4.5 |

Positive values for the temperature difference indicate the side rectifier (130) is warmer than the heavies column at the corresponding stage. Negative values for the temperature difference indicate the side rectifier (130) is cooler than the heavies column (110) at the corresponding stage.

The condenser (160), i.e., stage 1, of the side rectifier column (130) is not included in Table 3. Stages 2 to 11 of the side rectifier column (130) correspond to stages 18 to 27 of the heavies column (110), respectively. As can be seen in Table 3, the temperature difference between corresponding stages ranges from 3.9° F. (2.2° C.) warmer in the side rectifier column (130) to 6.8° F. (3.8° C.) cooler in the side rectifier column (130).

A graph of the temperature profile for the heavies column (110) and the side rectifier column (130) is shown in FIG. 3. The solid line labeled "MAIN" is the temperature profile for the heavies column (110). The dashed line labeled "SIDE" is the temperature profile for the side rectifier column (130). The temperature difference values listed in Table 3 between stages of the heavies column (110) and stages of the side rectifier column (130) can be seen in FIG. 3 as the vertical distance between the solid line labeled "MAIN" and the dashed line labeled "SIDE." As can be seen in FIG. 3, the temperature difference between corresponding stages ranges from 3.9° F. (2.2° C.) warmer in the side rectifier column (130) to 6.8° F. (3.8° C.) cooler in the side rectifier column (130).

The temperature profile for the side rectifier column in FIG. 3 is for internal placement. It is expected that an externally placed side rectifier column would have the same or similar temperature profile.

Table 4 below shows the operating conditions for the lights column system (120) of Example 1.

TABLE 4

Operating Conditions for Lights Column System in Example 1

| Stage (#) | Temperature (° F.) | Pressure (psig) | Net Feed (lbmol/hr) | Net Draw (lbmol/hr) | Duty (Btu/hr) |
|---|---|---|---|---|---|
| 1 | −20.0 | 319.0 | — | 929.3 | 563,284.7 |
| 2 | 89.7 | 319.0 | — | — | — |
| 3 | 133.7 | 319.5 | — | — | — |
| 4 | 148.9 | 320.0 | 5,086.8 | 4,157.5 | — |
| 5 | 153.9 | 320.0 | 115,965.8 | 5,086.8 | — |
| 6 | 156.5 | 320.3 | — | — | — |
| 7 | 160.4 | 320.5 | — | — | — |
| 8 | 164.0 | 320.8 | — | — | — |
| 9 | 166.1 | 321.1 | — | — | — |
| 10 | 167.2 | 321.3 | — | — | — |
| 11 | 167.8 | 321.6 | — | — | — |
| 12 | 168.2 | 321.8 | — | — | — |
| 13 | 168.5 | 322.1 | — | — | — |
| 14 | 168.8 | 322.4 | — | — | — |
| 15 | 169.1 | 322.6 | — | — | — |
| 16 | 169.5 | 322.9 | — | — | — |
| 17 | 169.9 | 323.2 | — | — | — |
| 18 | 170.4 | 323.4 | — | — | — |
| 19 | 170.9 | 323.7 | — | — | — |
| 20 | 171.5 | 323.9 | — | — | — |
| 21 | 172.3 | 324.2 | — | — | — |
| 22 | 173.7 | 324.5 | — | — | — |
| 23 | 176.7 | 324.7 | — | — | — |
| 24 | 183.4 | 325.0 | — | — | — |
| 25 | 196.8 | 325.0 | — | 110,879.0 | 4,033,751.9 |

In the model generated using the commercially available process modelling software, the lights column system (120) for Example 1 is two columns, a vent column (126) for which data in Table 4 is shown as stages 1 to 4, and a main column (122) for which data in Table 4 is shown as stages 5 to 26. As can be seen, 115,965.8 lbmol/hr (52,601.2 kgmol/hr) feeds to the main column (122). A net draw of 5,086.8 lbmol/hr (2,307.3 kgmol/hr) flows from the main column (122) to the vent column (126) in stream (124). The overhead stream (127) of the vent column (126) has a flow rate of 929.3 lbmol/hr (421.5 kgmol/hr). The bottoms stream (128) of the main column (122) recovers 110,879.0 lbmol/hr (50,293.9 kgmol/hr) for recycle to the polymerization process.

Stages 1 to 4 of the vent column (126) can function as the condenser for overhead stream (124) of the main column (122), and stage 25 is the reboiler (121) of the main column (122). Thus, the vent column (126) of Example 1's lights column system (120) has 4 internal stages (e.g., stages 1 to 4 in Table 4), and the main column (122) of Example 1's lights column system (120) has 20 internal stages (e.g., stages 5 to 24 in Table 4). Overall, the lights column system (120) of Example 1 (i.e., the main column (122) and vent column (126) combined) has 24 internal stages (e.g., stages 1 to 24 in Table 4). Stages of the lights column system (120), i.e., stages 1 to 24 operate at a temperature of from −20.0° F. (−28.9° C.) to 183.4° F. (84.1° C.) and a pressure of from 319.0 psig (2,199.4 kPag) to 325.0 psig (2,240.8 kPag). The reboiler (121) operates at a temperature of 196.8° F. (91.6° C.) and a pressure of 325.0 psig (2,240.8 kPag).

Figure 4:
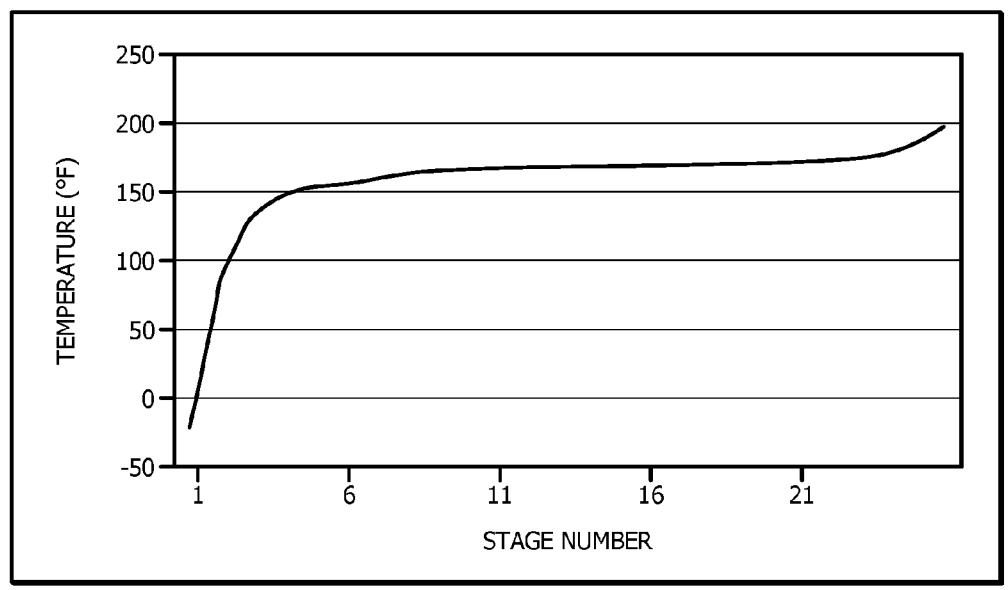
FIG. 4 is a graph of temperature versus stage number for a lights column in Example 1.
Figure 5:
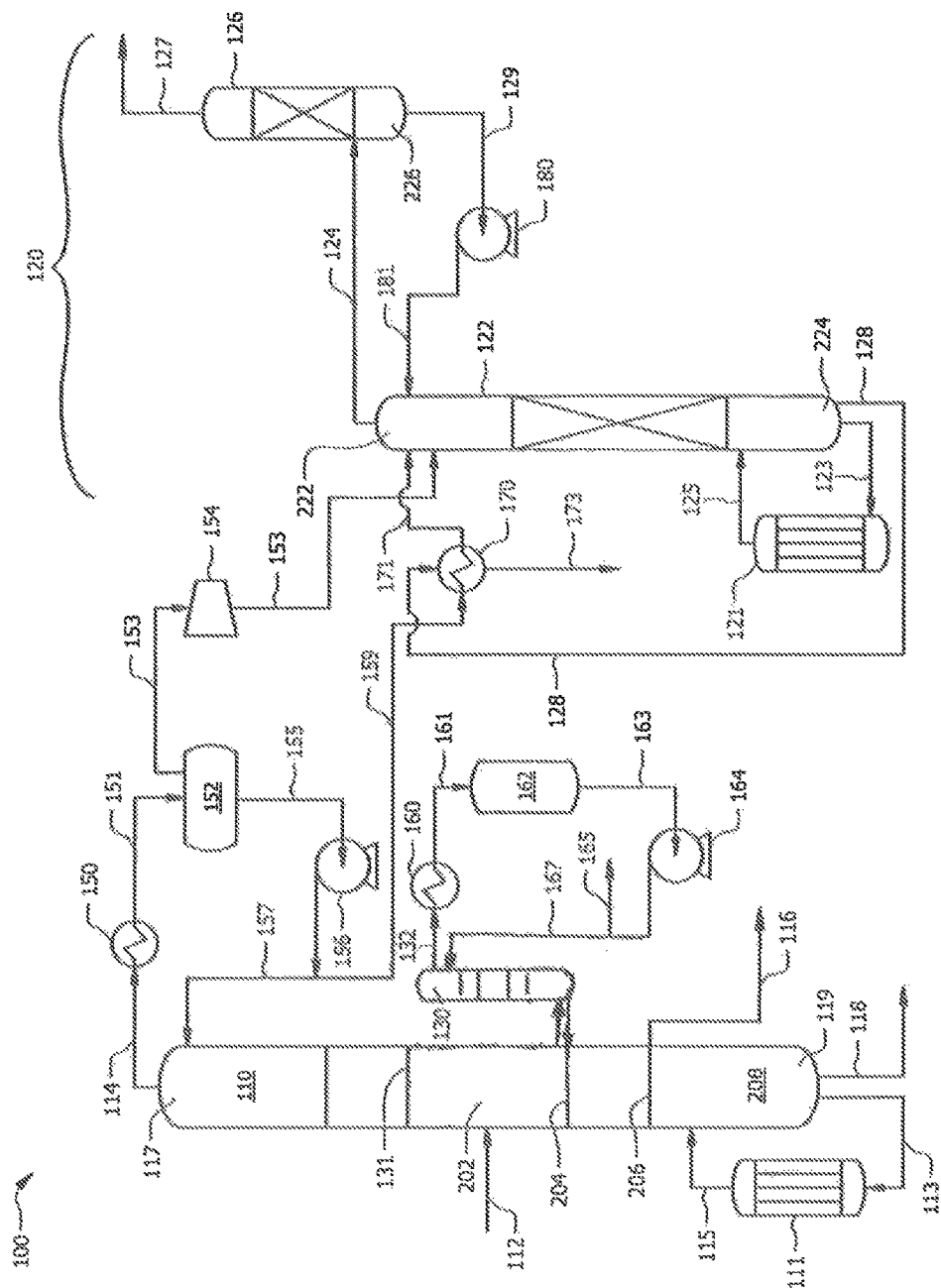
FIG. 5 illustrates an exemplary process flow diagram of an olefin and diluent recovery system similar to that presented in FIG. 1, utilizing a side rectifier column located externally of the heavies column.

A graph of the temperature profile for the lights column system (120) (the combined temperature profile of the main column (122) and vent column (126)) is shown in FIG. 4. As can be seen, the temperature in the vent column (126) quickly increases from −20.0° F. (−28.9° C.) at stage 1 to 148.9° F. (64.9° C.) at stage 4, and the temperature of the main column (122) increases more gradually from 153.9° F. (67.7° C.) at stage 5 to 173.7° F. (78.7° C.) at stage 22, with a more rapid increase in temperature from 173.7° F. (78.7° C.) at stage 22 to 196.8° F. (91.6° C.) at the reboiler.

ADDITIONAL DISCLOSURE

The following is provided as additional disclosure for combinations of features and aspects of the present invention.

Aspect 1 is a process comprising:
feeding isobutane, 1-hexene, and optionally one or more of hydrogen, nitrogen, ethane, and ethylene to a feed stage of a heavies column;
receiving isobutane and 1-hexene from an intermediate stage of the heavies column into a side rectifier column, the intermediate stage being between the feed stage and a recycle hexene takeoff stage of the heavies column;
recovering olefin-free isobutane from the side rectifier column;
recycling a first portion of the olefin-free isobutane to the side rectifier column as reflux; and
recycling a second portion of the olefin-free isobutane to a polymerization process.

Aspect 2 is the process of aspect 1, further comprising:
recovering isobutane and ethylene in an overhead stream of the heavies column; and
recovering a heavies purge bottoms stream of the heavies column.

Aspect 3 is the process of aspect 2, further comprising:
feeding the overhead stream of the heavies column to a lights column;
recovering ethylene in a bottoms stream of the lights column;
recovering isobutane in the bottoms stream of the lights column; and
recycling isobutane of the bottoms stream of the lights column to the polymerization process.

Aspect 4 is the process of aspect 3, wherein the lights column has no side draw stream between the overhead stream and the bottoms stream.

Aspect 5 is the process of any one of aspects 1-4, wherein olefin-free isobutane is recovered only from the side rectifier column.

Aspect 6 is the process of any one of aspects 3-5, wherein the isobutane in the bottoms stream of the lights column is not olefin-free isobutane.

Aspect 7 is the process of any one of aspects 1-6, wherein the side rectifier column is located internally of the heavies column and utilizes heat generated by a reboiler of the heavies column to recover the olefin-free isobutane.

Aspect 8 is the process of any one of aspects 1-7, wherein the side rectifier column is located externally of the heavies column.

Aspect 9 is the process of any one of aspects 1-8, wherein the second portion of the olefin-free isobutane comprises less than 1,000 ppmw 1-hexene based on a total weight of the second portion.

Aspect 10 is the process of any one of aspects 1-9, having an olefin efficiency of less than about 1.010.

Aspect 11 is the process of any one of aspects 1-10, further comprising:
feeding a fresh feed stream comprising fresh isobutane, fresh 1-hexene, and volatile components to a side degassing column, the side degassing column being positioned internally of the heavies column between the feed stage and the recycle hexene takeoff stage of the heavies column;
recovering the volatile components from an overhead stream of the side degassing column;
recycling a liquid phase recovered from the overhead stream of the side degassing column back to the side degassing column as reflux;
recovering 1-hexene in a bottoms stream of the side degassing column; and
flowing the bottoms stream of the side degassing column to a location external of the heavies column via the recycle hexene takeoff stage.

Aspect 12 is the process of aspect 11, wherein the side degassing column utilizes heat generated from a reboiler of the heavies column.

Aspect 13 is the process of any one of aspects 11-12, wherein the side rectifier column is located internally of the heavies column, wherein the bottom of the side degassing column is positioned closer to the recycle hexene takeoff stage than the bottom of the side rectifier column.

Aspect 14 is the process of any one of aspects 1-13, having at least a 30% reduction in energy consumption in comparison to an otherwise similar olefin and diluent recovery process not utilizing the side rectifier column in combination with the heavies column.

Aspect 15 is the process of any one of aspects 1-14, having at least a 30% reduction in energy consumption in comparison to an otherwise similar olefin and diluent recovery process that (a) does not utilize the side rectifier column in combination with the heavies column and (b) recovers olefin-free isobutane in the downstream lights column.

Aspect 16 is a process comprising:
feeding a fresh feed stream comprising fresh isobutane, fresh 1-hexene, and volatile components to a side degassing column, the side degassing column being positioned internally of a heavies column between a feed stage and a recycle hexene takeoff stage of the heavies column;
recovering the volatile components from an overhead stream of the side degassing column;
recycling a liquid phase recovered from the overhead stream of the side degassing column back to the side degassing column as reflux;
recovering 1-hexene in a bottoms stream of the side degassing column; and
flowing the bottoms stream of the side degassing column to a location external of the heavies column via the recycle hexene takeoff stage.

Aspect 17 is the process of aspect 16, wherein the side degassing column utilizes heat generated from a reboiler of the heavies column.

Aspect 18 is the process of any one of aspects 16-17, further comprising:
feeding isobutane and 1-hexene to the feed stage of the heavies column separately of the fresh isobutane, the fresh 1-hexene, and the volatile components fed to the side degassing column;
recovering an overhead stream comprising isobutane from the heavies column;
condensing the overhead stream of the heavies column to yield a liquid phase of isobutane; and recycling the liquid phase of isobutane to a polymerization process.

Aspect 19 is the process of aspect 18, wherein the step of recycling the liquid phase of isobutane to the polymerization process utilizes a lights column to remove hydrogen from the liquid phase of isobutane.

Aspect 20 is the process of any one of aspects 18-19, wherein the isobutane recycled to the polymerization process is not olefin-free isobutane.

Aspect 21 is the process of any one of aspects 16-20, further comprising:

receiving isobutane and 1-hexene from an intermediate stage of the heavies column into a side rectifier column, the intermediate stage being between the feed stage and the recycle hexene takeoff stage of the heavies column;

recovering olefin-free isobutane from the side rectifier column;

recycling a first portion of the olefin-free isobutane to the side rectifier column as reflux; and recycling a second portion of the olefin-free isobutane to the polymerization process.

Aspect 22 is the process of aspect 21, wherein olefin-free isobutane is recovered only from the side rectifier column.

Aspect 23 is the process of any one of aspects 21-22, wherein the side rectifier column is located internally of the heavies column and utilizes heat generated by a reboiler of the heavies column to recover the olefin-free isobutane, wherein the bottom of the side degassing column is positioned closer to the recycle hexene takeoff stage than the bottom of the side rectifier column.

Aspect 24 is the process of any one of aspects 21-23, wherein the side rectifier column is located externally of the heavies column.

Aspect 25 is the process of any one of aspects 21-24, wherein the second portion of the olefin-free isobutane comprises less than 1,000 ppmw 1-hexene based on a total weight of the second portion.

Aspect 26 is the process of any one of aspects 21-25, providing an olefin efficiency of less than about 1.010.

Aspect 27 is an olefin and diluent recovery system comprising:

a feed stream comprising isobutane, 1-hexene, and optionally one or more of hydrogen, ethane, nitrogen, and ethylene;

a heavies column receiving the feed stream and separating the feed stream into an overhead stream comprising isobutane and into a heavies purge bottoms stream comprising purge heavies;

a side rectifier column receiving isobutane and 1-hexene from an intermediate stage of the heavies column, the intermediate stage being between a feed stage and a recycle hexene takeoff stage of the heavies column; and an olefin-free isobutane stream flowing from the side rectifier column.

Aspect 28 is the olefin and diluent recovery system of aspect 27, further comprising:

a lights column receiving the overhead stream of the heavies column and separating the overhead stream of the heavies column to recover ethylene in an overhead stream of the lights column and to recover isobutane in a bottoms stream of the lights column, wherein the isobutane of the bottoms stream of the lights column is recycled to a polymerization process.

Aspect 29 is the olefin and diluent recovery system of aspect 28, wherein the lights column has no side draw stream between the overhead stream and the bottoms stream.

Aspect 30 is the olefin and diluent recovery system of any one of aspects 27-29, wherein olefin-free isobutane is recovered only from the side rectifier column.

Aspect 31 is the olefin and diluent recovery system of any one of aspects 28-30, wherein the isobutane of the bottoms stream of the lights column is not olefin-free isobutane.

Aspect 32 is the olefin and diluent recovery system of any one of aspects 27-31, wherein the olefin-free isobutane stream comprises less than 1,000 ppmw 1-hexene based on a total weight of the olefin-free isobutane stream.

Aspect 33 is the olefin and diluent recovery system of any one of aspects 27-32, which:

i) has at least a 30% reduction in energy consumption in comparison to an otherwise similar olefin and diluent recovery system not utilizing the side rectifier column in combination with the heavies column; or ii) has at least a 30% reduction in energy consumption in comparison to an otherwise similar olefin and diluent recovery system that (a) does not utilize the side rectifier column in combination with the heavies column and (b) recovers olefin-free isobutane in the downstream lights column.

Aspect 34 is the olefin and diluent recovery system of any one of aspects 27-33, providing an olefin efficiency of less than about 1.010.

Aspect 35 is the olefin and diluent recovery system of any one of aspects 27-34, further comprising:

a side degassing column receiving a fresh feed stream comprising fresh isobutane, fresh 1-hexene, and volatile components, the side degassing column being positioned internally of the heavies column and utilizing heat generated by a reboiler of the heavies column to separate the volatile components from the fresh isobutane and fresh 1-hexene.

Aspect 36 is the olefin and diluent recovery system of aspect 35, wherein the side degassing column has a bottoms stream comprising 1-hexene which flows from the side degassing column to a location external of the heavies column via the recycle hexene takeoff stage.

Aspect 37 is the olefin and diluent recovery system of any one of aspects 27-36, wherein the overhead stream of the heavies column is condensed to yield a liquid phase comprising isobutane, wherein the liquid phase is recycled to a polymerization process.

Aspect 38 is the olefin and diluent recovery system of aspect 37, wherein the liquid phase which is recycled to the polymerization process is not olefin-free isobutane.

Aspect 39 is the olefin and diluent recovery system of any one of aspects 35-38, wherein the side rectifier column is located internally of the heavies column, wherein the bottom of the side degassing column is positioned closer to the recycle hexene intermediate stage than the bottom of the side rectifier column.

Aspect 40 is an olefin and diluent recovery system comprising:

a first feed stream comprising isobutane and 1-hexene;

a heavies column receiving the first feed stream and separating the first feed stream into an overhead stream comprising isobutane and ethylene and a heavies purge bottoms stream comprising purge heavies;

a second feed stream comprising fresh isobutane, fresh 1-hexene, and volatile components; and a side degassing column receiving the second feed stream, the side degassing column being positioned internally of the heavies column and utilizing heat generated by a reboiler of the heavies column to separate the volatile components from the fresh isobutane and fresh 1-hexene received from the second feed stream.

Aspect 41 is the olefin and diluent recovery system of aspect 40, wherein the side degassing column has a bottoms stream comprising 1-hexene which flows from the side degassing column into the heavies column.

Aspect 42 is the olefin and diluent recovery system of any one of aspects 40-41, wherein the overhead stream of the heavies column is condensed to yield a liquid phase comprising isobutane, wherein the liquid phase is recycled to a polymerization process.

Aspect 43 is the olefin and diluent recovery system of aspect 42, wherein the isobutane of the liquid phase recycled to the polymerization process is not olefin-free isobutane.

Aspect 44 is the olefin and diluent recovery system of any one of aspects 40-43, further comprising:
a side rectifier column receiving isobutane and 1-hexene from an intermediate stage of the heavies column, the intermediate stage being between a feed stage and a recycle hexene takeoff stage of the heavies column; and
an olefin-free isobutane stream flowing from the side rectifier column.

Aspect 45 is the olefin and diluent recovery system of aspect 44, wherein olefin-free isobutane is recovered only from the side rectifier column.

Aspect 46 is the olefin and diluent recovery system of any one of aspects 44-45, wherein the olefin-free isobutane stream comprises less than 1,000 ppmw 1-hexene based on a total weight of the olefin-free isobutane stream.

Aspect 47 is the olefin and diluent recovery system of any one of aspects 44-46, having an olefin efficiency of less than about 1.010.

Aspect 48 is the olefin and diluent recovery system of any one of aspects 44-47, wherein the side rectifier column is located internally of the heavies column, wherein the bottom of the side degassing column is positioned closer to the recycle hexane takeoff stage than the bottom of the side rectifier column.

Aspect 49 is the olefin and diluent recovery system of any one of aspects 44-48, which:
i) has at least a 30% reduction in energy consumption in comparison to an otherwise similar olefin and diluent recovery system not utilizing the side rectifier column in combination with the heavies column; or
ii) has at least a 30% reduction in energy consumption in comparison to an otherwise similar olefin and diluent recovery system that (a) does not utilize the side rectifier column in combination with the heavies column and (b) recovers olefin-free isobutane in a downstream lights column.

Aspect 50 is the olefin and diluent recovery system of any one of aspects 40-49, further comprising:
a lights column receiving the overhead stream of the heavies column and separating the overhead stream of the heavies column to recover ethylene in an overhead stream of the lights column and to recover isobutane in a bottoms stream of the lights column, wherein the isobutane of the bottoms stream of the lights column is recycled to a polymerization process.

Aspect 51 is the olefin and diluent recovery system of aspect 50, wherein the lights column has no side draw stream between the overhead stream and the bottoms stream.

Aspect 52 is the olefin and diluent recovery system of any one of aspects 50-51, wherein olefin-free isobutane is recovered only from the side rectifier column.

Aspect 53 is the olefin and diluent recovery system of any one of aspects 50-52, wherein the isobutane of the bottoms stream of the lights column is not olefin-free isobutane.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15, . . . ). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention.

What is claimed is:

1. A process comprising:
feeding isobutane, 1-hexene, and optionally one or more of hydrogen, nitrogen, ethane, and ethylene to a feed stage of a heavies column;
receiving isobutane and 1-hexene from an intermediate stage of the heavies column into a side rectifier column, the intermediate stage being between the feed stage and a recycle hexene takeoff stage of the heavies column;
recovering olefin-free isobutane from the side rectifier column;
recycling a first portion of the olefin-free isobutane to the side rectifier column as reflux; and
recycling a second portion of the olefin-free isobutane to a polymerization process.

2. The process of claim 1, further comprising:
recovering isobutane and ethylene in an overhead stream of the heavies column; and
recovering a heavies purge bottoms stream of the heavies column.

3. The process of claim 2, further comprising:
feeding the overhead stream of the heavies column to a lights column;

recovering ethylene in a bottoms stream of the lights column;

recovering isobutane in the bottoms stream of the lights column; and recycling isobutane of the bottoms stream of the lights column to the polymerization process.

4. The process of claim 3, wherein the lights column has no side draw stream between the overhead stream and the bottoms stream.

5. The process of claim 3, wherein olefin-free isobutane is recovered only from the side rectifier column.

6. The process of claim 3, wherein the isobutane in the bottoms stream of the lights column is not olefin-free isobutane.

7. The process of claim 1, wherein the side rectifier column is located internally of the heavies column and utilizes heat generated by a reboiler of the heavies column to recover the olefin-free isobutane.

8. The process of claim 1, wherein the side rectifier column is located externally of the heavies column.

9. The process of claim 1, wherein the second portion of the olefin-free isobutane comprises less than 1,000 ppmw 1-hexene based on a total weight of the second portion.

10. The process of claim 1, having an olefin efficiency of less than about 1.010.

11. The process of claim 1, having at least a 30% reduction in energy consumption in an olefin and diluent recovery process not utilizing the side rectifier column in combination with the heavies column.

12. The process of claim 1, having at least a 30% reduction in energy consumption in comparison to an olefin and diluent recovery process that (a) does not utilize the side rectifier column in combination with the heavies column and (b) recovers olefin-free isobutane in a downstream lights column.

13. A process comprising:

feeding a fresh feed stream comprising fresh isobutane, fresh 1-hexene, and volatile components to a side degassing column, the side degassing column being positioned internally of a heavies column between a feed stage and a recycle hexene takeoff stage of the heavies column;

recovering the volatile components from an overhead stream of the side degassing column;

recycling a liquid phase recovered from the overhead stream of the side degassing column back to the side degassing column as reflux;

recovering 1-hexene in a bottoms stream of the side degassing column; and flowing the bottoms stream of the side degassing column to a location external of the heavies column via the recycle hexene takeoff stage.

14. The process of claim 13, wherein the side degassing column utilizes heat generated from a reboiler of the heavies column.

15. The process of claim 13, further comprising:

feeding isobutane and 1-hexene to the feed stage of the heavies column separately of the fresh isobutane, the fresh 1-hexene, and the volatile components fed to the side degassing column;

recovering an overhead stream comprising isobutane from the heavies column;

condensing the overhead stream of the heavies column to yield a liquid phase of isobutane; and recycling the liquid phase of isobutane to a polymerization process.

16. The process of claim 15, wherein the step of recycling the liquid phase of isobutane to the polymerization process utilizes a lights column to remove hydrogen from the liquid phase of isobutane.

17. The process of claim 15, wherein the isobutane recycled to the polymerization process is not olefin-free isobutane.

18. An olefin and diluent recovery system comprising:

a feed stream comprising isobutane, 1-hexene, and optionally one or more of hydrogen, ethane, nitrogen, and ethylene;

a heavies column receiving the feed stream and separating the feed stream into an overhead stream comprising isobutane and into a heavies purge bottoms stream comprising purge heavies;

a side rectifier column receiving isobutane and 1-hexene from an intermediate stage of the heavies column, the intermediate stage being between a feed stage and a recycle hexene takeoff stage of the heavies column; and an olefin-free isobutane stream flowing from the side rectifier column.

19. The olefin and diluent recovery system of claim 18, further comprising:

a lights column receiving the overhead stream of the heavies column and separating the overhead stream of the heavies column to recover ethylene in an overhead stream of the lights column and to recover isobutane in a bottoms stream of the lights column, wherein the isobutane of the bottoms stream of the lights column is recycled to a polymerization process.

20. An olefin and diluent recovery system comprising:

a first feed stream comprising isobutane and 1-hexene;

a heavies column receiving the first feed stream and separating the first feed stream into an overhead stream comprising isobutane and ethylene and a heavies purge bottoms stream comprising purge heavies;

a second feed stream comprising fresh isobutane, fresh 1-hexene, and volatile components; and a side degassing column receiving the second feed stream, the side degassing column being positioned internally of the heavies column and utilizing heat generated by a reboiler of the heavies column to separate the volatile components from the fresh isobutane and fresh 1-hexene received from the second feed stream.

\* \* \* \* \*